United States Patent
Miyazaki

(10) Patent No.: US 8,947,730 B2
(45) Date of Patent: Feb. 3, 2015

(54) COLORIMETRIC APPARATUS AND COLORIMETRIC METHOD

(71) Applicant: Canon Kabushiki Kaisha, Tokyo (JP)

(72) Inventor: Toshiki Miyazaki, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 2 days.

(21) Appl. No.: 13/782,466

(22) Filed: Mar. 1, 2013

(65) Prior Publication Data

US 2013/0258366 A1   Oct. 3, 2013

(30) Foreign Application Priority Data

Mar. 27, 2012   (JP) .................................. 2012-072338

(51) Int. Cl.
| | |
|---|---|
| G06F 15/00 | (2006.01) |
| G06K 1/00 | (2006.01) |
| G01J 3/46 | (2006.01) |
| B41F 33/00 | (2006.01) |
| G01J 3/10 | (2006.01) |
| G01J 3/50 | (2006.01) |
| G01N 21/35 | (2014.01) |
| G01N 21/89 | (2006.01) |
| G01J 3/02 | (2006.01) |

(52) U.S. Cl.
CPC . *G01J 3/46* (2013.01); *B41F 33/00* (2013.01); *G01J 3/10* (2013.01); *G01J 3/50* (2013.01); *G01N 21/35* (2013.01); *G01N 21/89* (2013.01); *G01J 3/027* (2013.01); *G01J 2003/468* (2013.01)

USPC .......................................................... 358/1.9

(58) Field of Classification Search
None
See application file for complete search history.

(56) References Cited

U.S. PATENT DOCUMENTS

| | | | |
|---|---|---|---|
| 5,636,015 A | 6/1997 | Imura et al. | |
| 8,456,709 B2 | 6/2013 | Uratani et al. | |
| 2005/0190400 A1* | 9/2005 | Redd et al. | 358/1.15 |
| 2009/0237682 A1* | 9/2009 | Bala et al. | 358/1.9 |
| 2011/0149319 A1* | 6/2011 | Muto et al. | 358/1.9 |
| 2012/0044497 A1* | 2/2012 | Totsuka | 356/402 |
| 2012/0195498 A1 | 8/2012 | Miyazaki et al. | |
| 2012/0218572 A1 | 8/2012 | Kishino et al. | |

FOREIGN PATENT DOCUMENTS

JP        08-313349 A        11/1996

* cited by examiner

*Primary Examiner* — Benny Q Tieu
*Assistant Examiner* — Michael Burleson
(74) *Attorney, Agent, or Firm* — Fitzpatrick, Cella, Harper & Scinto

(57) ABSTRACT

In an apparatus including an irradiation unit capable of irradiating a sheet selectively with visible light and ultraviolet light, and a measurement unit which measures a spectral reflectance based on light reflected by the sheet, whether to cause the irradiation unit to emit the ultraviolet light when measuring the spectral reflectance of a patch image printed on the sheet is determined based on the spectral reflectance of a reference image of the color of the sheet that has been measured by the measurement unit which measures a spectral reflectance while the ultraviolet light is emitted.

6 Claims, 14 Drawing Sheets

| INDEX | PAPER WHITE FLAG |
|---|---|
| 0 | 1 |
| 1 | 0 |
| .... | .... |
| N-1 | 0 |

1301

COLORIMETRIC APPARATUS AND COLORIMETRIC METHOD

BACKGROUND OF THE INVENTION

1. Field of the Invention

The present invention relates to a colorimetric apparatus and colorimetric method capable of colorimetry.

2. Description of the Related Art

Applying a fluorescent brightener to a sheet (printing medium) such as printing paper in order to improve the brightness is known. The fluorescent brightener has a characteristic of emitting light in the visible light wavelength range upon receiving irradiation of light outside visible light wavelengths, typified by ultraviolet rays. Thus, the color reproduction of an image output from a printing apparatus changes depending on an observation light source. In a printing apparatus using a sheet containing a fluorescent brightener, colorimetry is sometimes performed by measuring the spectral radiance factor of light generated by the fluorescent brightener, in order to faithfully estimate the reproduction color of an output image under an arbitrary observation light source.

A total spectral radiance factor representing the color of a sample under an arbitrary observation light source is obtained by compositing a reflection spectral radiance factor containing no fluorescence of the sample and a fluorescence spectral radiance factor serving as a fluorescent component. To acquire the total spectral radiance factor of a sample, it is necessary to acquire two spectral radiance factors respectively describing the reflection spectral radiance factor containing no fluorescent component of the sample, and the fluorescence spectral radiance factor serving as the fluorescent component.

In general, to acquire these two spectral radiance factors, a sample is irradiated with two or more types of light sources including a white light source having wavelengths in the visible light range and an ultraviolet light source having wavelengths in the ultraviolet light range, and the spectral radiance factor of the sample is detected using a spectral radiance meter for each light source. Japanese Patent Laid-Open No. 08-313349 discloses a method of measuring spectral radiance factors of a sample under two types of light sources, that is, a light source containing ultraviolet light and a light source containing no ultraviolet light, multiplying the measured spectral wavelengths by load coefficients, and compositing them, thereby obtaining the total spectral radiance factor of the sample.

In the sheet colorimetric method disclosed in Japanese Patent Laid-Open No. 08-313349, measurement needs to be executed while switching the plurality of types of light sources regardless of whether or not the sheet contains a fluorescent brightener. For a sheet containing no fluorescent brightener, no spectral radiance factor need be measured under the ultraviolet light source essentially, and this measurement generates an unwanted measurement time.

SUMMARY OF THE INVENTION

An aspect of the present invention is to eliminate the above-mentioned problems with the conventional technology. The present invention provides a colorimetric apparatus and colorimetric method for performing efficient colorimetry in accordance with a sheet.

The present invention in its first aspect provides a colorimetric apparatus comprising: an irradiation unit configured to irradiate a sheet selectively with visible light and ultraviolet light; a measurement unit configured to measure a spectral reflectance based on light reflected by the sheet; and a determination unit configured to determine, based on a spectral reflectance of a reference image of a color of the sheet that is measured by the measurement unit while the ultraviolet light is emitted, whether to cause the irradiation unit to emit the ultraviolet light when measuring a spectral reflectance of a patch image printed on the sheet.

The present invention in its second aspect provides a colorimetric method comprising: a first measurement step of measuring a spectral reflectance of a reference image of a color of a sheet while irradiating the sheet with ultraviolet light; a second measurement step of measuring a spectral reflectance of a patch image printed on the sheet while irradiating the sheet with visible light; and a determination step of determining, based on whether the spectral reflectance measured in the first measurement step contains a spectral reflectance of a wavelength region of visible light, whether to measure the spectral reflectance of the patch image while irradiating the sheet with ultraviolet light.

According to the present invention, efficient colorimetry can be performed in accordance with a sheet.

Further features of the present invention will become apparent from the following description of exemplary embodiments with reference to the attached drawings.

DESCRIPTION OF THE EMBODIMENTS

Figure 1:
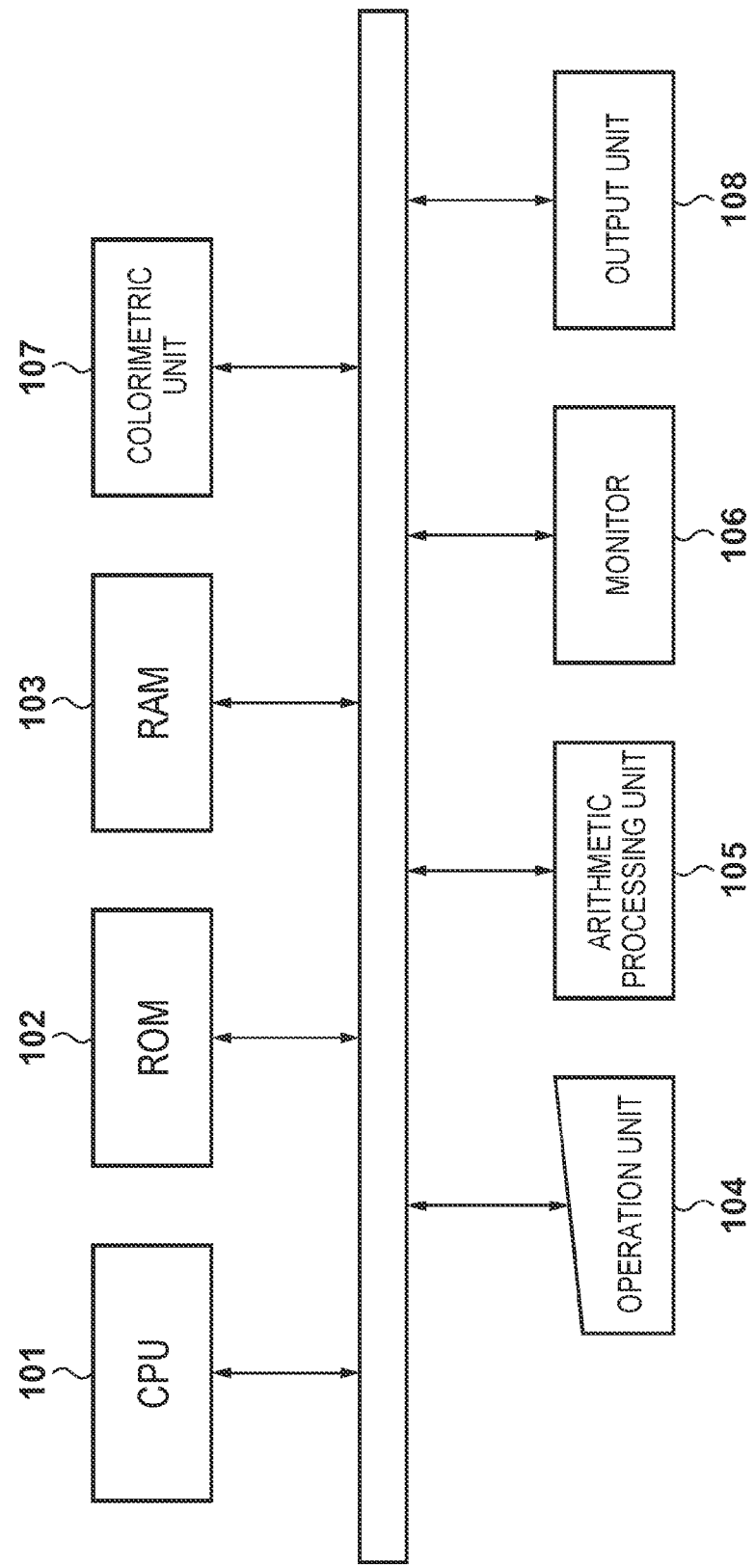
FIG. 1 is a block diagram showing a hardware arrangement in a printing apparatus.

Preferred embodiments of the present invention will now be described hereinafter in detail, with reference to the accompanying drawings. It is to be understood that the following embodiments are not intended to limit the claims of the present invention, and that not all of the combinations of the aspects that are described according to the following embodiments are necessarily required with respect to the means to solve the problems according to the present invention. Note that the same reference numerals denote the same parts, and a repetitive description thereof will be omitted.

[Arrangement of Printing Apparatus]

The embodiment uses a printing apparatus which prints an image on a sheet serving as a printing medium based on image data. Although a printing apparatus including a measurement apparatus which measures the color of the patch image of a patch chart will be described below, the printing apparatus and measurement apparatus may be separated. The printing apparatus suffices to print an image on a sheet, and, for example, an inkjet printing apparatus is used. The arrangement of the inkjet printing apparatus as an example of the printing apparatus will be described later.

FIG. 1 is a block diagram showing a hardware arrangement in the printing apparatus. A CPU 101 in the printing apparatus controls a RAM 103, operation unit 104, arithmetic processing unit 105, monitor (display unit) 106, colorimetric (color measuring) unit 107, and output unit 108 in accordance with control programs stored in a ROM 102, an operating system, application programs, device drivers, and the like. These units are connected via a bus to be able to communicate with each other. The colorimetric unit 107 is, for example, the measurement apparatus which measures the color of a patch image printed on a sheet (sample). The output unit 108 prints an image on a sheet based on image data. The RAM 103 is used as a work area and temporary save area when executing various control programs or processing data input from the operation unit 104. The operation unit 104 accepts, for example, an instruction from the user to execute a measurement operation and printing operation by the colorimetric unit 107 and output unit 108. The arithmetic processing unit 105 calculates the spectral radiance factor of the fluorescent component of a sample and that of the sample under an observation light source, which will be described later. The monitor 106 displays the arithmetic result of the arithmetic processing unit 105, data input from the operation unit 104, and the like.

In the embodiment, both the luminance factor of a light source and the luminance factor of a sample irradiated by the light source will be called spectral radiance factors. However, the luminance factor of a sample will also be called "spectral reflectance" by paying attention to the reflectance of irradiation light. From the viewpoint of colorimetry in the embodiment, the spectral radiance factor and the spectral reflectance are synonymous. The sample is a sheet on which a patch image is printed. In the embodiment, the printing apparatus handles a sheet containing a fluorescent brightener and one containing no fluorescent brightener.

Figure 2:
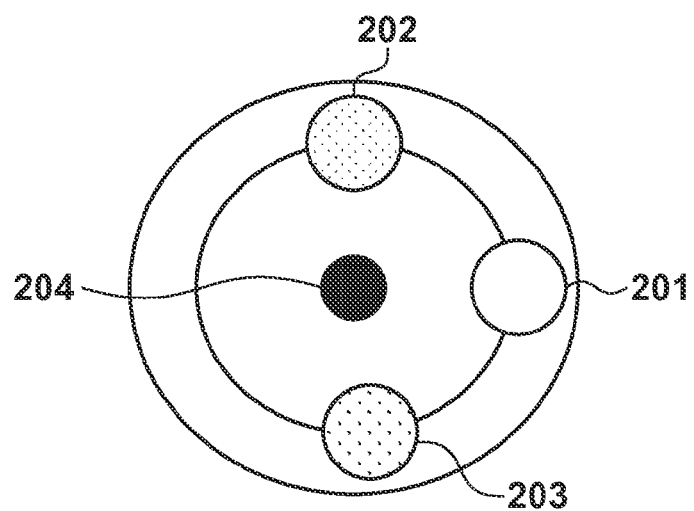
FIG. 2 is a view showing the arrangement of measurement light sources and a sensor arranged in a measurement apparatus.
Figure 3:
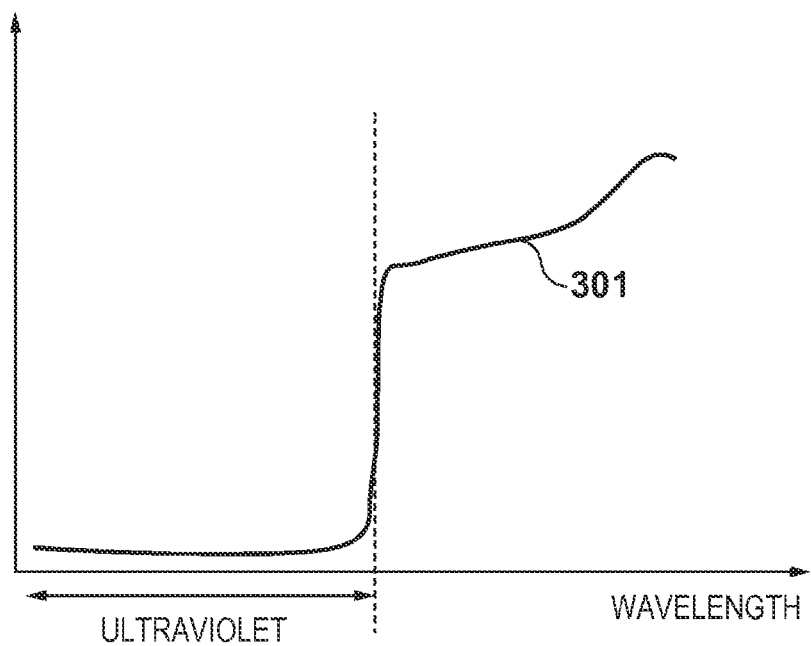
FIG. 3 is a graph showing an example of the spectral radiance factor of a white light source.
Figure 4:
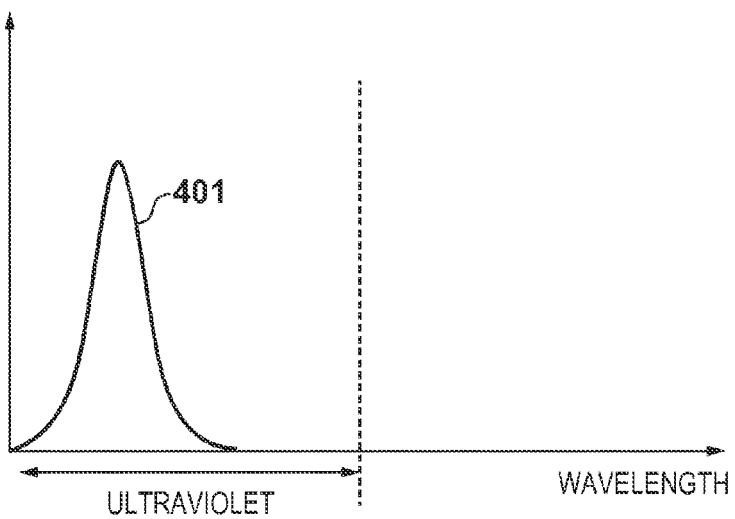
FIG. 4 is a graph showing an example of the spectral radiance factor of an ultraviolet light source.
Figure 5:
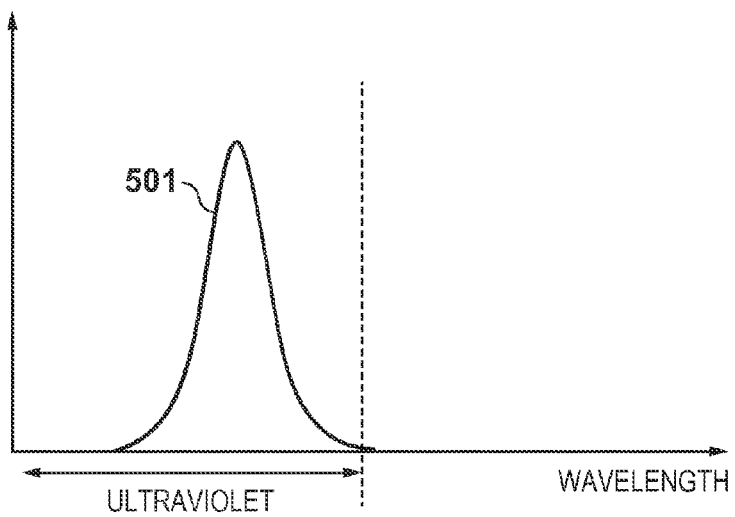
FIG. 5 is a graph showing another example of the spectral radiance factor of an ultraviolet light source.

FIG. 2 is a view showing the arrangement of measurement light sources and a sensor arranged in the measurement apparatus within the printing apparatus. In the embodiment, a white light source 201 (first light source), and ultraviolet light sources 202 and 203 (second light source) are used as measurement light sources. The white light source 201 emits light of wavelengths in the visible light range containing no ultraviolet rays. The ultraviolet light source 202 (first ultraviolet light source) and the ultraviolet light source 203 (second ultraviolet light source) emit beams of different ultraviolet wavelengths. A sensor 204 detects the spectral radiance factor of a sample under each measurement light source. FIG. 3 is a graph exemplifying the spectral radiance factor of the white light source 201. As shown in FIG. 3, a spectral radiance factor 301 of the white light source 201 does not contain ultraviolet wavelengths, and contains only wavelengths in the visible light range. FIG. 4 is a graph exemplifying the spectral radiance factor of the ultraviolet light source 202. FIG. 5 is a graph exemplifying the spectral radiance factor of the ultraviolet light source 203. As shown in FIGS. 4 and 5, the two types of ultraviolet light sources 202 and 203 are different in the peak wavelength of the spectral radiance factor and the spectral radiance factor distribution. Both the ultraviolet light sources do not contain wavelengths in the visible light range.

Figure 6:
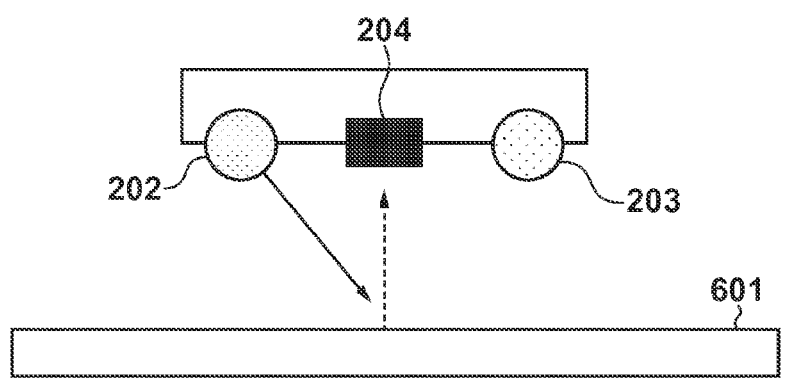
FIG. 6 is a view for explaining a sample measurement method by the measurement apparatus.

FIG. 6 is a view for explaining a method of measuring the spectral radiance factor of a sample by the measurement apparatus arranged in the printing apparatus. At least one of the white light source 201 and the ultraviolet light sources 202 and 203 is turned on and irradiates a sample 601. The sensor 204 receives a spectral radiation from the sample as a result of irradiating the sample with each ON light source, and acquires a spectral radiance factor for each light source.

Figure 7:
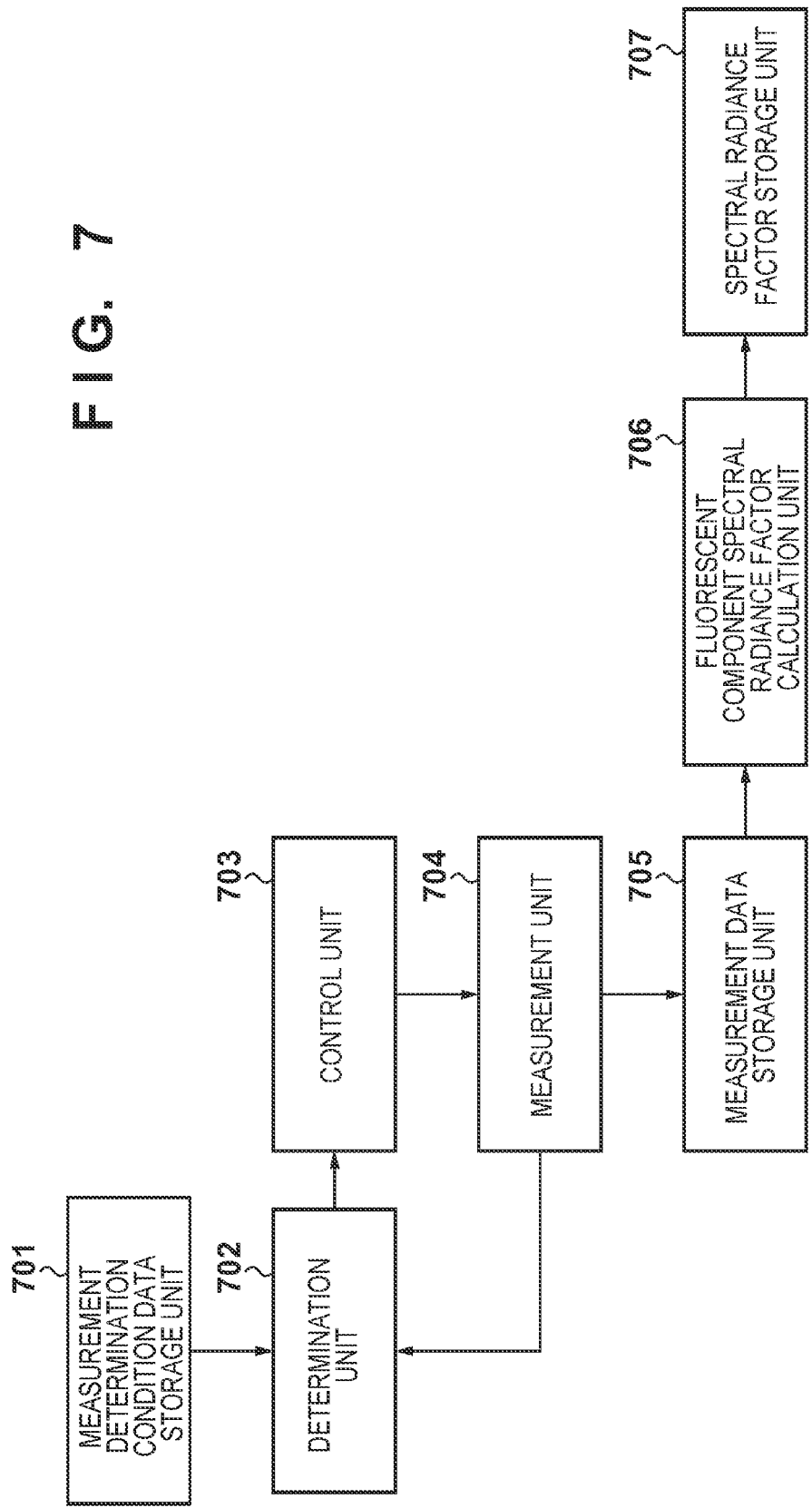
FIG. 7 is a block diagram showing the functional arrangement of the measurement apparatus in the printing apparatus.

FIG. 7 is a block diagram showing the functional arrangement of the measurement apparatus in the printing apparatus. A measurement unit 704 measures the spectral radiance factor of a sample by using each measurement light source and the sensor. A control unit 703 controls emission of each measurement light source. A measurement determination condition data storage unit 701 stores a condition to determine which of the ultraviolet light sources 202 and 203 is used. By referring to the determination condition, a determination unit 702 determines whether to turn on the ultraviolet light sources 202 and 203. A measurement data storage unit 705 stores a spectral radiance factor measured by the measurement unit 704 for each measurement light source. A fluorescent component spectral radiance factor calculation unit 706 calculates the spectral radiance factor of the fluorescent component of the sample from spectral radiance factors measured using the ultraviolet light sources 202 and 203. A spectral radiance factor storage unit 707 stores the spectral radiance factor of the visible light component of the sample measured under the white light source 201, and the spectral radiance factor of the fluorescent component calculated by the fluorescent component spectral radiance factor calculation unit 706.

Figure 8:
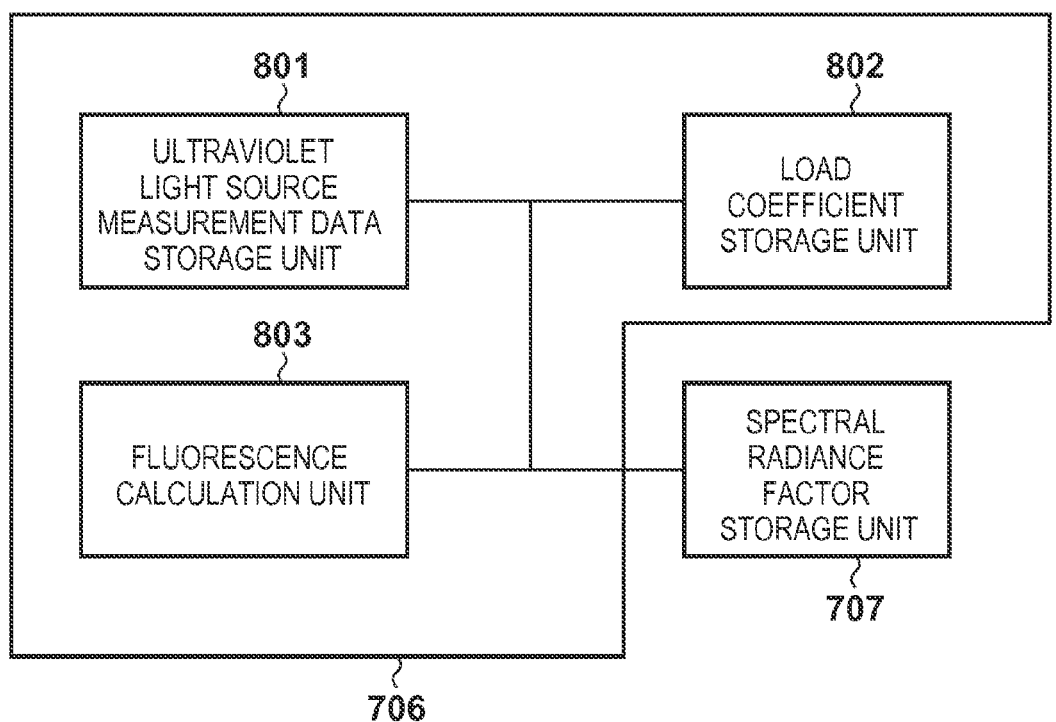
FIG. 8 is a block diagram showing the arrangement of a fluorescent component spectral radiance factor calculation unit.
Figure 9:
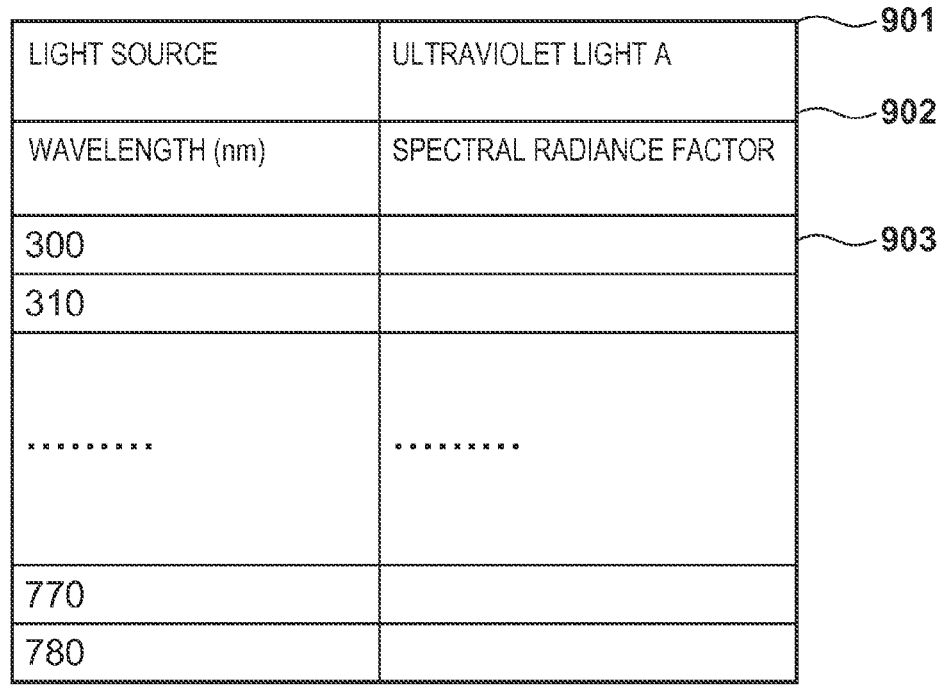
FIG. 9 is a table showing a memory configuration which stores the spectral radiance factor of the fluorescent component.
Figure 10:
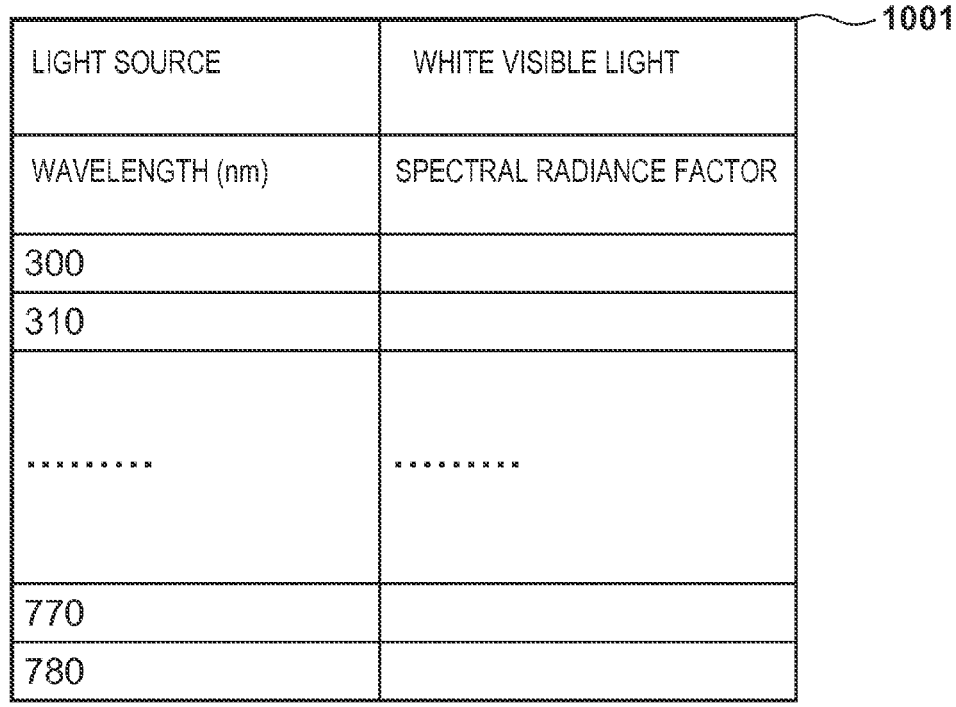
FIG. 10 is a table showing a memory configuration which stores the spectral radiance factor of the visible light component.

FIG. 8 is a block diagram showing the arrangement of the fluorescent component spectral radiance factor calculation unit 706. An ultraviolet light source measurement data storage unit 801 stores the spectral radiance factor of a sample measured by the measurement unit 704 under each ultraviolet light source. FIG. 9 is a table exemplifying a memory configuration which stores a spectral radiance factor. A spectral radiance factor storage memory 901 includes a light source information memory 902 which stores the type of measurement light source, and a spectral radiance factor memory 903 which stores a spectral radiance factor in correspondence with each discrete input wavelength. The spectral radiance factor storage unit 707 stores the spectral radiance factor of the sample measured under the white light source 201 in a spectral radiance factor data storage memory 1001 as shown in FIG. 10. The spectral radiance factor data storage memory 1001 has the same configuration as that of the spectral radiance factor storage memory 901 shown in FIG. 9.

A fluorescence calculation unit 803 in FIG. 8 calculates the spectral radiance factor of the fluorescent component of a sample by compositing spectral radiance factors of the sample measured under the ultraviolet light sources 202 and 203 by using load coefficients corresponding to the respective ultraviolet light sources. A load coefficient storage unit 802 stores the load coefficients corresponding to the respective ultraviolet light sources to be used in the fluorescence calculation unit 803. In the embodiment, the load coefficients are set in advance for the respective ultraviolet light sources. The spectral radiance factor of the fluorescent component obtained by the composite operation of the fluorescence calculation unit 803 is stored in the spectral radiance factor storage unit 707 in the same format as that in the spectral radiance factor storage memory 901 shown in FIG. 9.

Next, a method of calculating the spectral radiance factor of the fluorescent component by the fluorescence calculation unit 803 will be explained. In the embodiment, the two types of ultraviolet light sources 202 and 203 are used as measurement light sources. $I1(\lambda)$ and $I2(\lambda)$ are spectral radiance factors of a sample that are measured by the two types of ultraviolet light sources 202 and 203, respectively. A spectral radiance factor $F(\lambda)$ of the fluorescent component of the sample is calculated according to equation (1) using load coefficients $W1$ and $W2$ corresponding to the ultraviolet light sources 202 and 203, respectively:

$$F(\lambda) = I1(\lambda) \times W1 + I2(\lambda) \times W2 \quad (1)$$

wherein the load coefficients $W1$ and $W2$ are values independent of the observation light source of a sample.

Next, a method of calculating a total spectral radiance factor $T(\lambda)$ of a sample under an arbitrary observation light source will be explained. $S0(X)$ is the spectral radiance factor of the white light source 201, and $I0(\lambda)$ is the spectral radiance factor of a sample measured under the white light source 201. Then, a spectral radiance factor $R(\lambda)$ of the visible light component of the sample under an arbitrary observation light source is calculated from a spectral radiance factor $S(\lambda)$ the observation light source according to equation (2):

$$R(\lambda) = S(\lambda) \cdot I0(\lambda)/S0\lambda) \quad (2)$$

From this, the total spectral radiance factor $T(\lambda)$ of the sample under the arbitrary observation light source is calculated as the sum of the visible light component and fluorescent component according to equation (3):

$$T(\lambda) = R(\lambda) + F(\lambda) = S(\lambda) \times I0(\lambda)/S0(\lambda) + I1(\lambda) \times W1 + I2(\lambda) \times W2 \quad (3)$$

[Processing Sequence from Patch Image Printing to Colorimetry]

Figure 11:
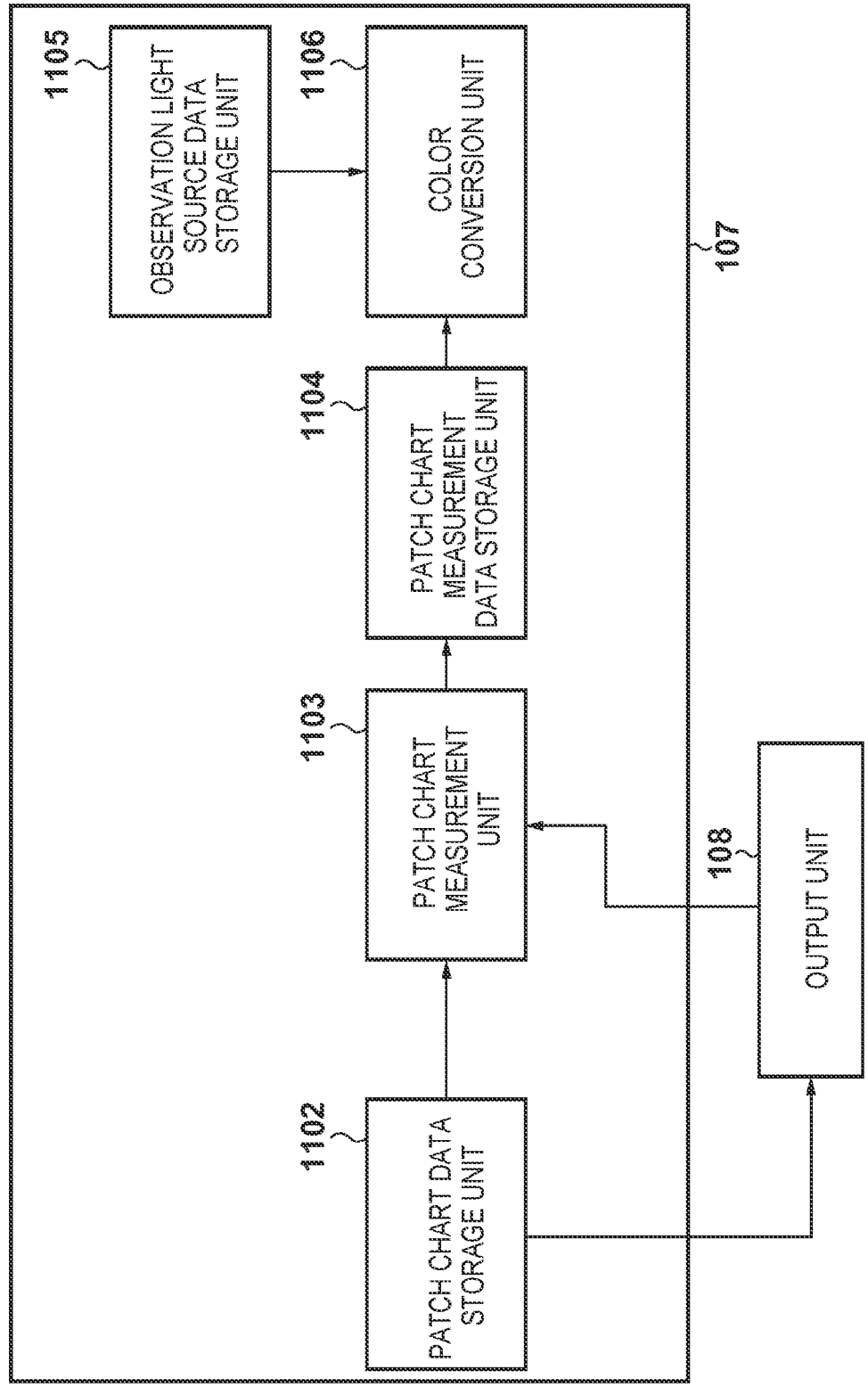
FIG. 11 is a block diagram for explaining a processing sequence from printing of a patch image up to colorimetry.

FIG. 11 is a block diagram for explaining a processing sequence from printing of a patch image on a sheet up to colorimetry in the printing apparatus. A patch chart data storage unit 1102 in the measurement apparatus serving as the colorimetric unit 107 stores patch chart data for measuring the output characteristics of the printing apparatus in output profile creation, calibration, or the like, and measurement condition data representing a paper white flag corresponding to each patch image on the patch chart.

Figures 12, 13:
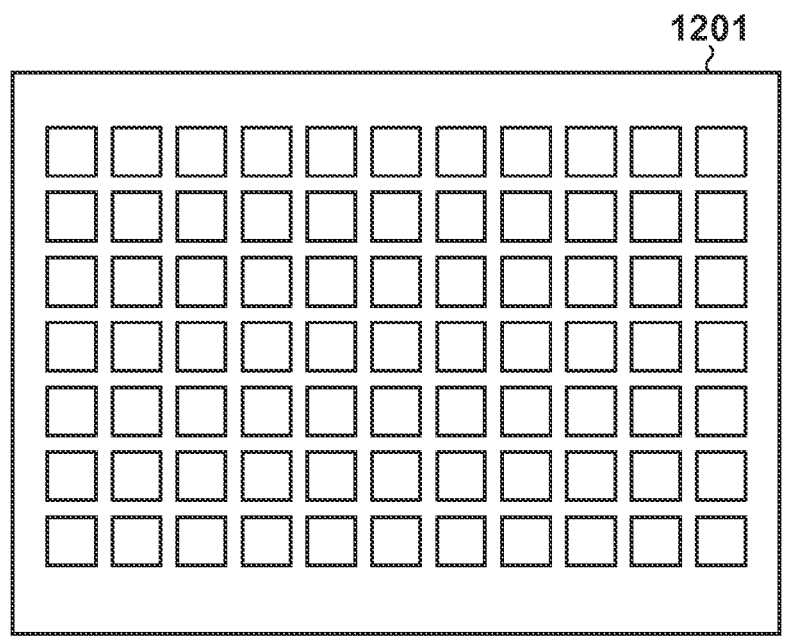
FIG. 12 is a view exemplifying a patch chart.
FIG. 13 is a table exemplifying a paper white position flag.

FIG. 12 is a view exemplifying a patch chart. A patch chart 1201 is formed from a plurality of color chips (patch images) obtained by combining discrete values of input signals (R, G, and B signals or C, M, Y, and K signals) to the printing apparatus. In FIG. 12, an upper left patch image is a reference patch image of paper white, that is, a sheet color where no ink is applied. Colorimetry by the measurement apparatus starts from the reference patch image and sequentially proceeds rightward. After the end of measuring one line, the target returns to a patch image at the left end on an immediately lower line, and colorimetry is executed similarly.

The output unit 108 prints a patch chart on a sheet based on patch chart data input from the patch chart data storage unit 1102. A patch chart measurement unit 1103 performs colorimetry for each color chip on the patch chart. First, the patch chart measurement unit 1103 recognizes the position of the reference patch image by referring to the paper white flag representing that a patch image on the patch chart acquired from the patch chart data storage unit 1102 is paper white. The patch chart measurement unit 1103 measures the spectral radiance factor of the reference patch image by using the ultraviolet light sources 202 and 203 (example of reference measurement). In accordance with the measurement result, the patch chart measurement unit 1103 controls the ON operation of the ultraviolet light sources 202 and 203 in colorimetry of another patch image.

FIG. 13 is a table exemplifying the paper white flag. In a measurement condition memory 1301, a color chip of paper white is indicated by a flag in correspondence with an index corresponding to the alignment of N color chips to be measured on the patch chart. As described above, since the first patch image at an upper left position in FIG. 12 is paper white, a flag value corresponding to the index "0" in FIG. 13 is "1", and those corresponding to the remaining indices are "0". The flag shown in FIG. 13 may be automatically determined from the result of analyzing patch chart data and registered when the user registers the patch chart data, or may be registered by prompting the user to select a color chip he wants.

The patch chart measurement unit 1103 stores, in the measurement determination condition data storage unit 701, data of the paper white flag acquired from the patch chart data storage unit 1102. First, the control unit 703 controls the measurement unit 704 to measure the spectral radiance factor of the reference patch image having the paper white flag "1" by using the ultraviolet light sources 202 and 203. In accordance with the measurement result, the determination unit 702 determines the presence/absence of a fluorescent brightener in the sheet on which the reference patch image is printed, and determines whether to use the ultraviolet light sources 202 and 203 when the measurement unit 704 sequentially measures the colors of the remaining color chips. In colorimetry of each color chip, the control unit 703 controls the ON operation of each measurement light source in accordance with the determination result of the determination unit 702.

The measurement unit 704 measures not only spectral radiance factors of a sample under the ultraviolet light sources 202 and 203, but also a spectral radiance factor of the sample under the white light source 201. The fluorescent component spectral radiance factor calculation unit 706 calculates the spectral radiance factor of the fluorescent component of the sample by compositing spectral radiance factors measured using the ultraviolet light sources 202 and 203 by using predetermined load coefficients for the respective ultraviolet light sources. A patch chart measurement data storage unit 1104 stores the calculated spectral radiance factor of the fluorescent component and the spectral radiance factor of the sample measured under the white light source 201.

A color conversion unit 1106 calculates the total spectral radiance factor of the sample under an observation light source in accordance with equations (2) and (3) by using the spectral radiance factor of the fluorescent component and the spectral radiance factor of the sample measured under the white light source 201 which are stored in the patch chart measurement data storage unit 1104. Further, the color conversion unit 1106 converts the calculated total spectral radiance factor into a chromaticity value in CIELab or the like (example of chromaticity acquisition). In the embodiment, processing up to conversion from a spectral radiance factor into a chromaticity value is especially called colorimetry. An observation light source data storage unit 1105 stores in advance the spectral radiance factors ($S(\lambda)$ in equation (2)) of respective measurement light sources and various observation light sources.

[Calculation of Total Spectral Radiance Factor of Sample under Observation Light Source]

Figure 14:
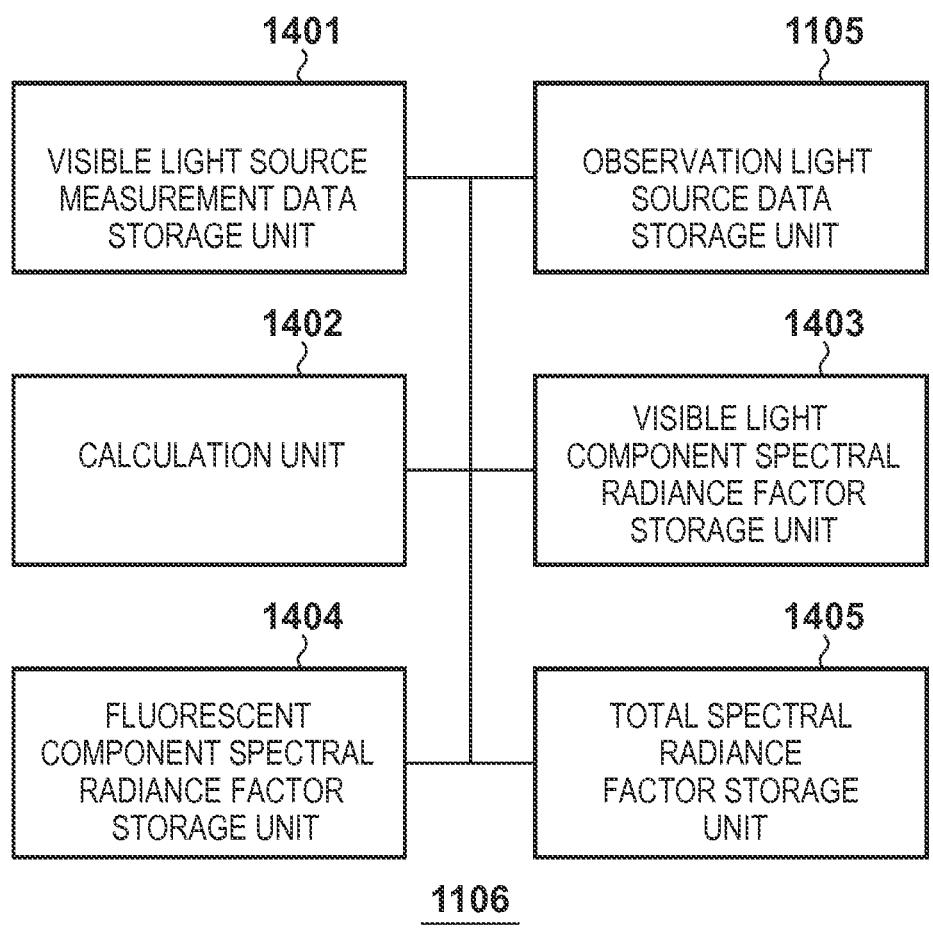
FIG. 14 is a block diagram showing an arrangement for calculating the total spectral radiance factor of a sample under an observation light source.

FIG. 14 is a block diagram showing an arrangement for calculating the total spectral radiance factor of a sample under an observation light source in the color conversion unit 1106. A visible light source measurement data storage unit 1401 stores a spectral radiance factor which has been measured under the white light source 201 and acquired from the patch chart measurement unit 1103. A fluorescent component spectral radiance factor storage unit 1404 stores the spectral radiance factor of the fluorescent component of a sample which has been measured by the patch chart measurement unit 1103 and calculated by the fluorescence calculation unit 803.

A calculation unit 1402 integrates the spectral radiance factor of an observation light source acquired by the observation light source data storage unit 1105 and the spectral radiance factor of a sample measured under the white light source 201, divides the sum by the spectral radiance factor of the observation light source, and stores the result as the spectral radiance factor of the visible light component of the sample under the observation light source in a visible light component spectral radiance factor storage unit 1403. Further, the calculation unit 1402 calculates the total spectral radiance factor of the sample under the observation light source by compositing, in accordance with equation (3), the spectral radiance factor of the fluorescent component and that of the visible light component of the sample which are stored in the fluorescent component spectral radiance factor storage unit 1404. A total spectral radiance factor storage unit 1405 stores the calculated total spectral radiance factor of the sample under the observation light source. The color conversion unit 1106 converts the total spectral radiance factor of the sample under the observation light source into a chromaticity value in CIELab or the like, which is then stored in a chromaticity value storage unit (not shown).

[Measurement of Spectral Radiance Factor for Each Color Chip]

Figure 15:
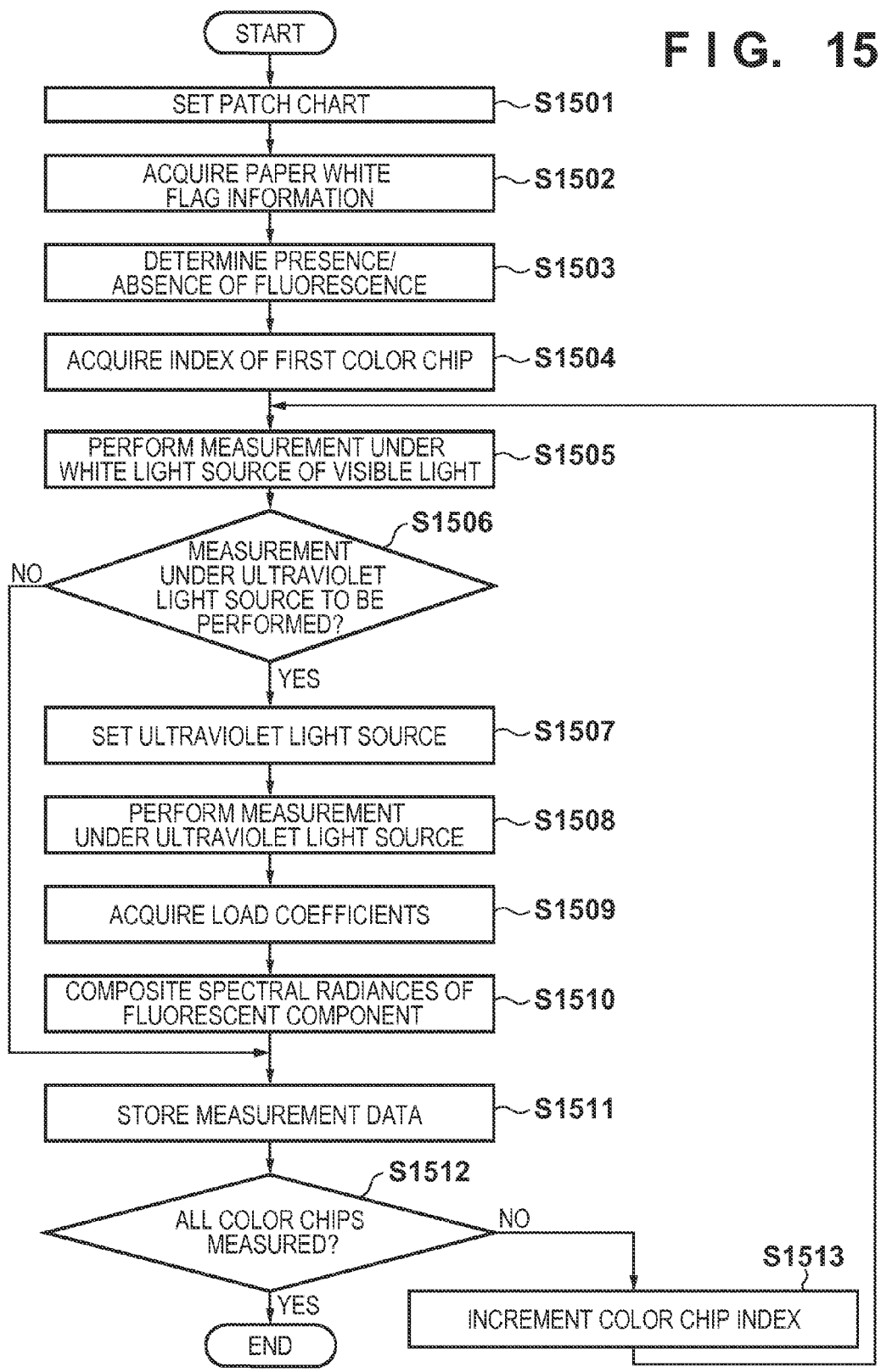
FIG. 15 is a flowchart showing the sequence of a spectral radiance factor measurement method.

FIG. 15 is a flowchart showing the sequence of a spectral radiance factor measurement method in the embodiment. Respective processes shown in FIG. 15 are implemented by, for example, executing the units in FIGS. 7, 8, 11, and 14 by the CPU 101 of the printing apparatus. In step S1501, the user sets, in the measurement unit 704 of the measurement apparatus, a patch chart which has been printed on a sheet by the output unit 108. In step S1502, the CPU 101 acquires paper white flag information corresponding to each color chip on the set patch chart, and specifies a color chip (reference patch image) representing paper white. In step S1503, the spectral radiance factor of the reference patch image is measured using the ultraviolet light sources 202 and 203, and it is determined whether the sheet contains a fluorescent brightener.

Figure 17:
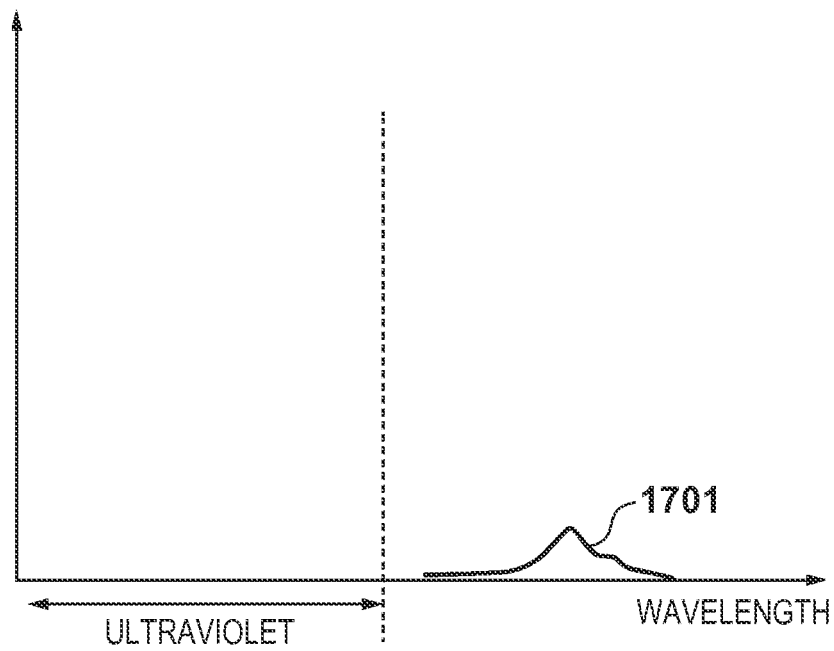
FIG. 17 is a graph showing a spectral radiance factor when a sheet contains a fluorescent brightener.
Figure 18:
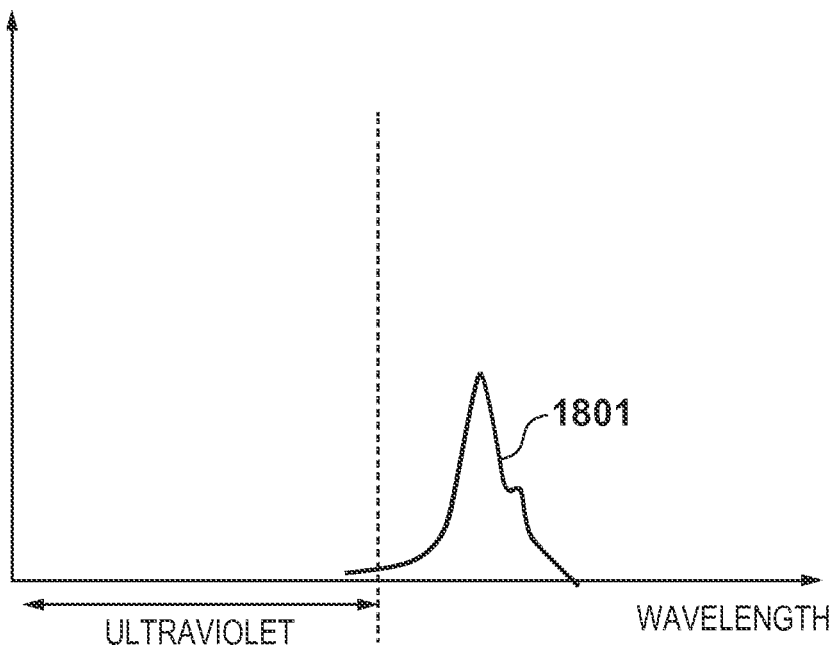
FIG. 18 is a graph showing another spectral radiance factor when a sheet contains a fluorescent brightener.

FIGS. 17 and 18 are views for explaining determination of whether the sheet contains a fluorescent brightener. In general, the ultraviolet light sources 202 and 203 have energy only in the ultraviolet light range, as shown in FIGS. 4 and 5. However, it is generally known that, when a sheet containing a fluorescent brightener is irradiated with ultraviolet light, light of a bluish color is generated. That is, a gain is generated in the visible light wavelength band, as shown in FIGS. 17 and 18. The embodiment utilizes this phenomenon, and when reflected light is observed in the visible light range in response to irradiation of ultraviolet light, it is determined that the sheet contains a fluorescent brightener.

In step S1504, the CPU 101 acquires the index of a color chip serving as the first colorimetric target. In step S1505, the color of the color chip is measured under the white light source 201. The colorimetric operation is the same as that described with reference to FIG. 11. In step S1506, the CPU 101 determines, in accordance with the result of determining the presence/absence of the fluorescent brightener in step S1503, whether to measure the spectral radiance factor of the fluorescent component of the colorimetric target color chip. If the sheet contains the fluorescent brightener, the CPU 101 determines to measure the spectral radiance factor of the fluorescent component of the colorimetric target color chip. If the CPU 101 determines in step S1506 to measure the spectral radiance factor of the fluorescent component, it sets the ultraviolet light source in step S1507. In this case, if a plurality of ultraviolet light sources are designated, processes in subsequent steps are executed while sequentially switching the ultraviolet light sources in measurement in the respective steps.

In step S1508, the CPU 101 measures the spectral radiance factor of the color chip under each ultraviolet light source set in step S1507. In step S1509, the CPU 101 acquires a load coefficient corresponding to each ultraviolet light source. In step S1510, the CPU 101 performs a composite operation based on the spectral radiance factors measured for the respective ultraviolet light sources in step S1508 and the load coefficients acquired in step S1509, and calculates the spectral radiance factor of the fluorescent component of the sample. In step S1511, the spectral radiance factor of the fluorescent component calculated in step S1510 and the spectral radiance factor measured under the white light source 201 in step S1505 are stored. If the CPU 101 determines in step S1506 not to measure the spectral radiance factor of the fluorescent component, only the spectral radiance factor measured under the white light source 201 in step S1505 is stored.

In step S1512, the CPU 101 determines whether all the color chips of the set patch chart have been measured. If the CPU 101 determines that all the color chips have not been measured, it increments the index in step S1513 to set a color chip serving as the next measurement target, and repeats the processing from step S1505.

Although measurement using each ultraviolet light source is performed after measurement using the white light source 201 in FIG. 15, the measurement may be executed in the reverse order. The processing in FIG. 15 has been explained by exemplifying the printing apparatus integrated with the measurement apparatus. However, the processing in FIG. 15 may be performed by the single measurement apparatus as long as a patch chart printed by a separate printing apparatus is used.

[Calculation of Total Spectral Radiance Factor under Arbitrary Observation Light Source]

Figure 16:
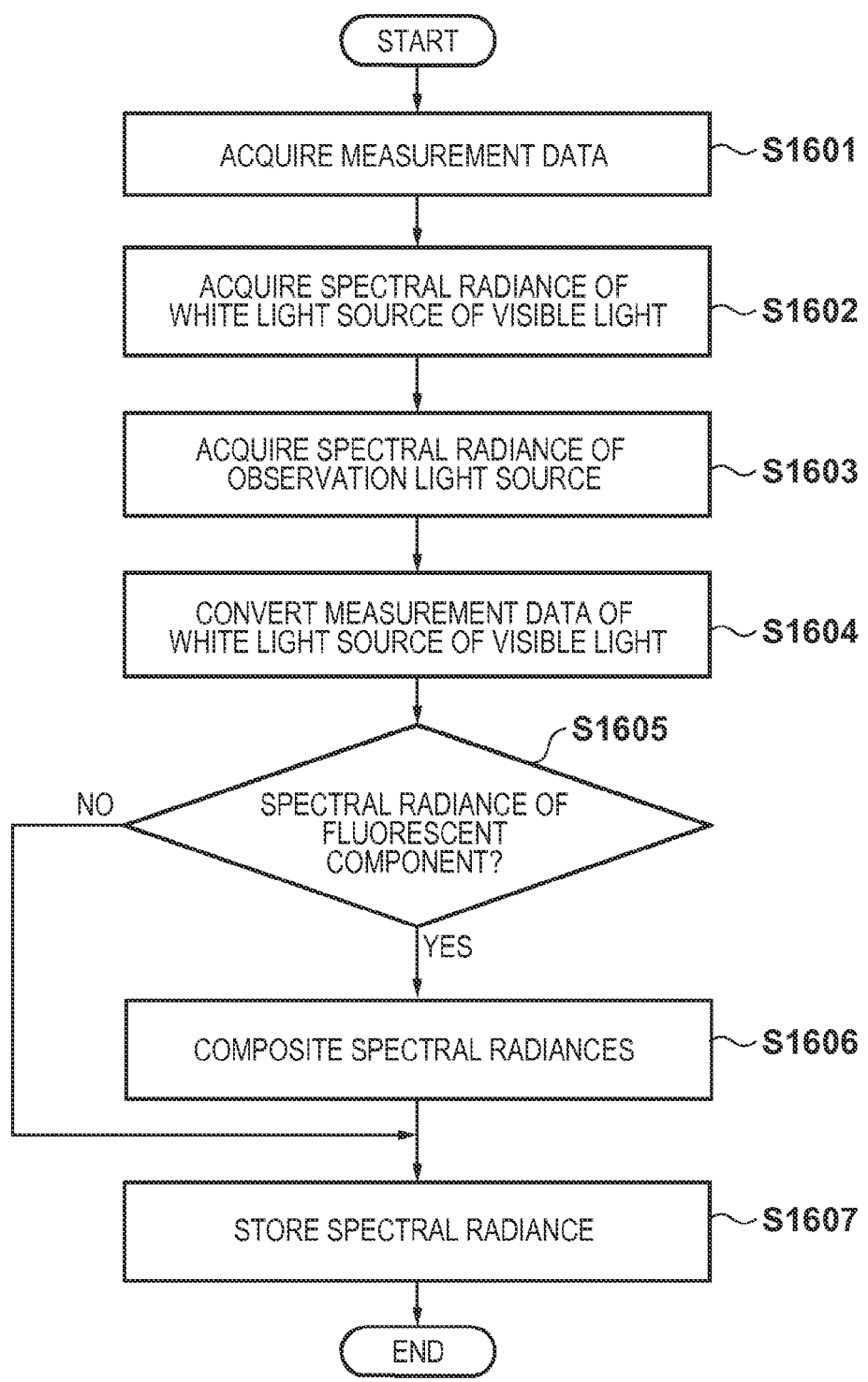
FIG. 16 is a flowchart showing a processing sequence to calculate a total spectral radiance factor under an observation light source.

FIG. 16 is a flowchart showing a processing sequence to calculate a total spectral radiance factor under an arbitrary observation light source from the spectral radiance factors of respective color chips acquired in FIG. 15. Respective processes shown in FIG. 16 are implemented by, for example, executing the units in FIGS. 7, 8, 11, and 14 by the CPU 101 of the printing apparatus. In step S1601, the CPU 101 acquires a measured spectral radiance factor of the fluorescent component and a spectral radiance factor measured under the white light source 201 for one color chip. The CPU 101 acquires the spectral radiance factor of the white light source 201 in step S1602, and acquires the spectral radiance factor of the observation light source in step S1603.

In step S1604, the CPU 101 calculates the spectral radiance factor of the visible light component for the color chip in accordance with equation (2) from the spectral radiance factors of the white light source 201 and observation light source, and the spectral radiance factor measured under the white light source 201. In step S1605, the CPU 101 determines whether the measurement results acquired in step S1601 include the spectral radiance factor of the fluorescent component. If the CPU 101 determines in step S1605 that the measurement results include the spectral radiance factor of the fluorescent component, it calculates a total spectral radiance factor under the observation light source by compositing the spectral radiance factor of the visible light component calculated in step S1604 and the spectral radiance factor of the fluorescent component acquired in step S1601 in accordance with equation (3) in step S1606. In step S1607, the total spectral radiance factor under the observation light source calculated in step S1606 is stored.

If the CPU 101 determines in step S1605 that the measurement results do not include the spectral radiance factor of the fluorescent component, it stores in step S1607 only the spectral radiance factor of the visible light component calculated in step S1604.

As described above, the spectral radiance factor of the fluorescent component arising from a fluorescent brightener can be efficiently acquired when measuring the spectral radiance factor of a sample in profile creation processing or calibration in the printing apparatus. The target of colorimetry which takes time because the ultraviolet light source is used can be limited to only a sheet containing a fluorescent brightener, and efficient measurement can be executed.

Next, the arrangement of the inkjet printing apparatus as an example of the printing apparatus in the embodiment will be explained. It is also possible to execute colorimetry and perform the processes in FIGS. 15 and 16 by combining the measurement apparatus described in the embodiment with the inkjet printing apparatus to be described below.

[Description of Inkjet Printing Apparatus]

Figure 19:
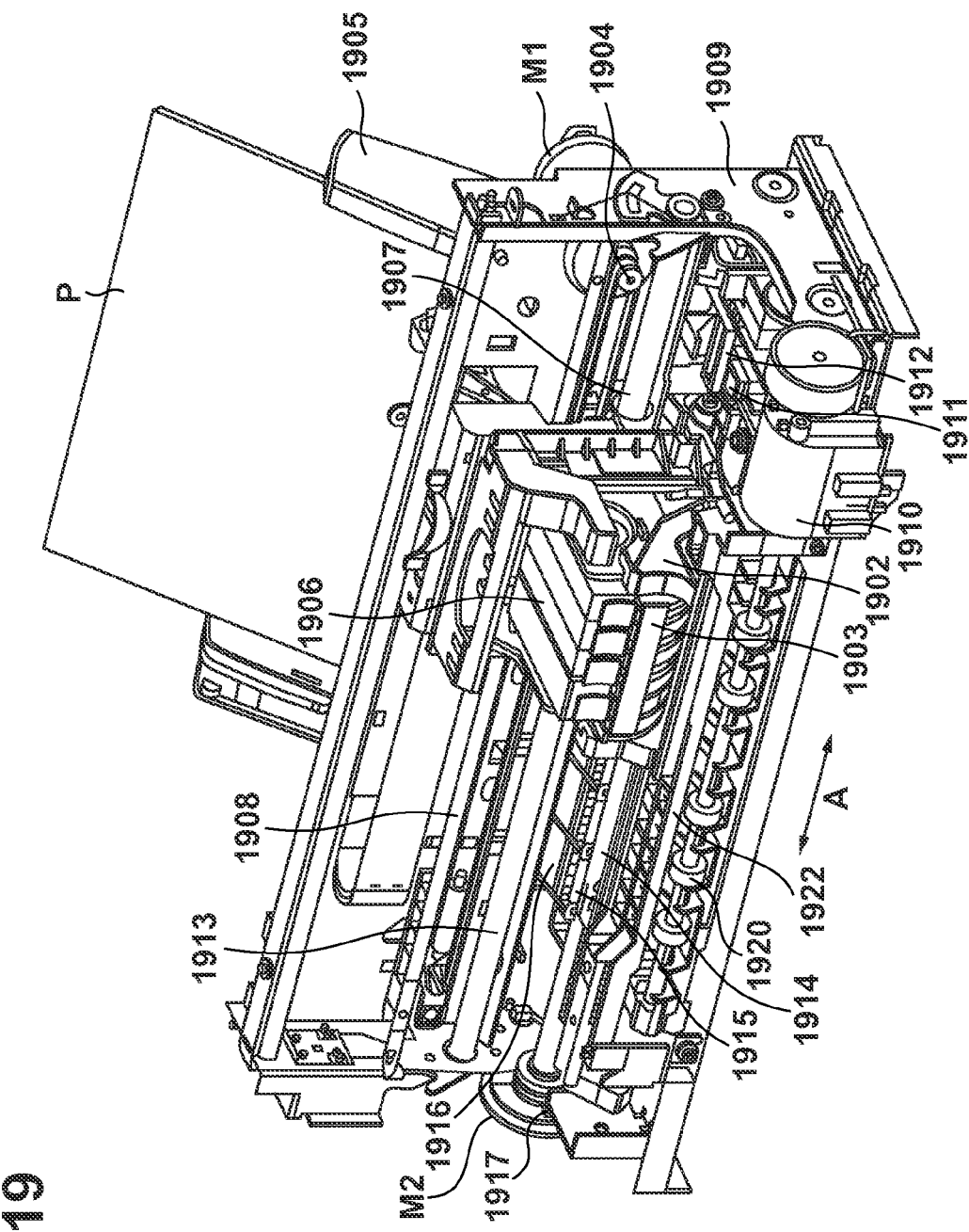
FIG. 19 is a perspective view showing the arrangement of an inkjet printing apparatus.

FIG. 19 is an outer perspective view showing the schematic arrangement of the inkjet printing apparatus as a typical embodiment of the present invention.

The inkjet printing apparatus shown in FIG. 19 prints as follows. A transmission mechanism 1904 transmits a driving force generated by a carriage motor M1 to a carriage 1902 which supports a printhead 1903 for printing by discharging ink according to an inkjet method, thereby reciprocating the carriage 1902 in directions indicated by an arrow A. At the same time, a sheet P such as a piece of printing paper is fed via a paper feed mechanism 1905, and conveyed to a printing position. At the printing position, the printhead 1903 discharges ink onto the sheet P.

To maintain a good state of the printhead 1903, the carriage 1902 is moved to the position of a recovery device 1910 to intermittently execute discharge recovery processing for the printhead 1903.

In addition to the printhead 1903, an ink cartridge 1906 which stores ink to be supplied to the printhead 1903 is mounted on the carriage 1902 of the inkjet printing apparatus. The ink cartridge 1906 is detachable from the carriage 1902.

The inkjet printing apparatus shown in FIG. 19 can print in color. For this purpose, four ink cartridges which store magenta (M), cyan (C), yellow (Y), and black (K) inks, respectively, are mounted on the carriage 1902. These four ink cartridges are independently detachable.

The carriage 1902 and printhead 1903 can achieve and maintain necessary electrical connection by properly bringing their joint surfaces into contact with each other. By applying energy in accordance with a print signal, the printhead 1903 prints by selectively discharging ink from a plurality of orifices. Especially, the printhead 1903 in the embodiment employs an inkjet method of discharging ink using thermal energy. The printhead 1903 includes electrothermal transducers for generating thermal energy. Electrical energy applied to the electrothermal transducers is converted into thermal energy. Ink is discharged from orifices using a pressure change caused by growth and contraction of bubbles generated by film boiling upon applying the thermal energy to ink. The electrothermal transducers are arranged in correspondence with respective orifices. By applying a pulse voltage to a corresponding electrothermal transducer in accordance with a print signal, ink is discharged from a corresponding orifice. Note that the inkjet method is not limited to this, and is arbitrarily a method using a piezoelectric element, one using a MEMS element, or one using an electrostatic element.

As shown in FIG. 19, the carriage 1902 is coupled to part of a driving belt 1907 of the transmission mechanism 1904 which transmits the driving force of the carriage motor M1. The carriage 1902 is guided and supported slidably along a guide shaft 1913 in the directions indicated by the arrow A. The carriage 1902 reciprocates along the guide shaft 1913 by forward rotation and reverse rotation of the carriage motor M1. A scale 1908 (CR encoder film) is arranged in the moving direction (directions indicated by the arrow A) of the carriage 1902 to indicate the absolute position of the carriage 1902. In the embodiment, the scale 1908 is formed by printing black bars at necessary pitches on a transparent PET film. One end of the scale 1908 is fixed to a chassis 1909, and the other end is supported by a leaf spring (not shown).

In the inkjet printing apparatus, a platen (not shown) is arranged to face the orifice surface of the printhead 1903 on which orifices (not shown) are formed. Simultaneously when the carriage 1902 supporting the printhead 1903 is reciprocated by the driving force of the carriage motor M1, a print signal is supplied to the printhead 1903 to discharge ink, thereby printing at the full width on the sheet P conveyed onto the platen.

A conveyance motor M2 drives a conveyance roller 1914 in FIG. 19 to convey the sheet P. A pinch roller 1915 makes the sheet P abut against the conveyance roller 1914 by a spring (not shown). A pinch roller holder 1916 rotatably supports the pinch roller 1915. A conveyance roller gear 1917 is fixed to one end of the conveyance roller 1914. The conveyance roller 1914 is driven by rotation of the conveyance motor M2 that is transmitted to the conveyance roller gear 1917 via an intermediate gear (not shown).

A discharge roller 1920 discharges, from the inkjet printing apparatus, the sheet P bearing an image formed by the printhead 1903. The discharge roller 1920 is driven by transmitting rotation of the conveyance motor M2. The discharge roller 1920 abuts against a spur roller (not shown) which press-contacts the sheet P by a spring (not shown). A spur holder 1922 rotatably supports the spur roller.

In the inkjet printing apparatus, as shown in FIG. 19, the recovery device 1910 for recovering the printhead 1903 from a discharge failure is arranged at a desired position (for example, a position corresponding to the home position) outside the range (outside the printing region) of reciprocating motion for the printing operation of the carriage 1902 on which the printhead 1903 is mounted.

The recovery device 1910 includes a capping mechanism 1911 which caps the orifice surface of the printhead 1903, and a wiping mechanism 1912 which cleans the orifice surface of the printhead 1903. The recovery device 1910 performs discharge recovery processing. More specifically, ink is forcibly discharged from orifices by a suction arrangement (for example, a suction pump) in the recovery device in synchronism with capping of the orifice surface by the capping mechanism 1911. This removes viscosity-increased ink, bubbles, and the like in the ink channel of the printhead 1903.

In a non-printing operation or the like, the capping mechanism 1911 caps the orifice surface of the printhead 1903 so that the printhead 1903 can be protected, and evaporation and drying of ink can be prevented. The wiping mechanism 1912 is arranged near the capping mechanism 1911, and wipes ink droplets attached to the orifice surface of the printhead 1903.

The capping mechanism 1911 and wiping mechanism 1912 can normally maintain the ink discharge state of the printhead 1903.

[Control Arrangement of Inkjet Printing Apparatus]

Figure 20:
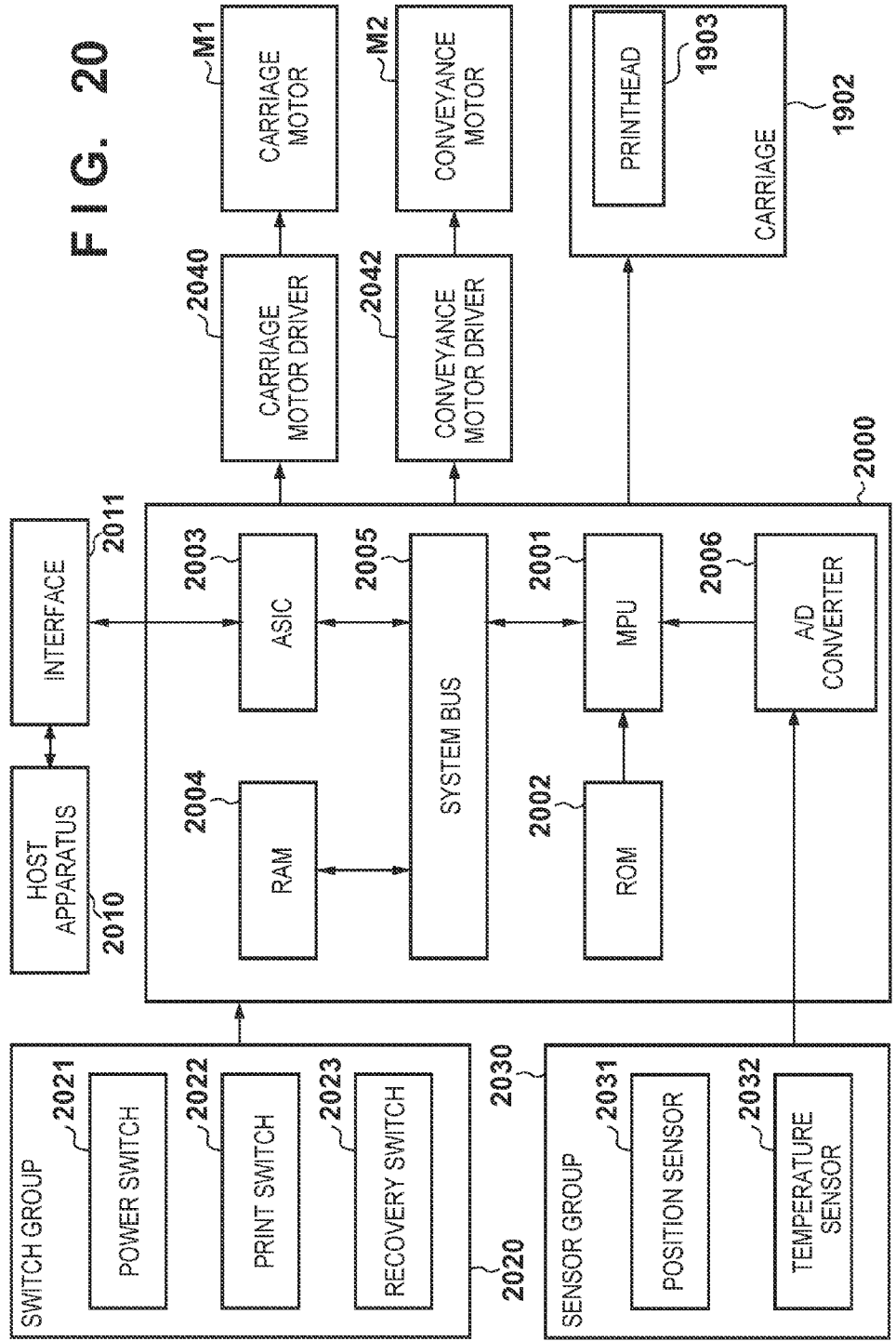
FIG. 20 is a block diagram showing the control arrangement of the inkjet printing apparatus.

FIG. 20 is a block diagram showing the control arrangement of the inkjet printing apparatus shown in FIG. 19.

As shown in FIG. 20, a control unit 2000 includes an MPU 2001, ROM 2002, application specific integrated circuit (ASIC) 2003, RAM 2004, system bus 2005, and A/D converter 2006. The ROM 2002 stores programs corresponding to control sequences (to be described later), necessary tables, and other permanent data. The ASIC 2003 generates control signals to control the carriage motor M1, conveyance motor M2, and printhead 1903. The RAM 2004 provides an image data rasterization area, a work area for executing a program, and the like. The system bus 2005 connects the respective blocks to each other to exchange data. The A/D converter 2006 receives an analog signal from a sensor group (to be described later), A/D-converts it, and supplies the digital signal to the MPU 2001.

Referring to FIG. 20, a host apparatus 2010 is a computer (or a reader for reading an image, a digital camera, or the like) serving as an image data supply source. The host apparatus 2010 and inkjet printing apparatus transmit/receive image data, commands, status signals, and the like to/from each other via an interface (I/F) 2011.

A switch group 2020 includes switches for accepting instruction inputs by the operator, such as a power switch 2021, a print switch 2022 for instructing the start of printing, and a recovery switch 2023 for designating activation of processing (recovery processing) for maintaining good ink discharge performance of the printhead 1903. A sensor group 2030 includes sensors for detecting the state of the inkjet printing apparatus, such as a position sensor 2031 (for example, a photocoupler) for detecting the home position, and a temperature sensor 2032 arranged at an appropriate portion in the inkjet printing apparatus to detect the ambient temperature.

A carriage motor driver 2040 drives the carriage motor M1 to reciprocally scan the carriage 1902 in the directions indicated by the arrow A shown in FIG. 19. A conveyance motor driver 2042 drives the conveyance motor M2 to convey the sheet P.

At the time of print scanning by the printhead 1903, the ASIC 2003 transfers printing element (discharge heater) driving data to the printhead while directly accessing the storage area of the ROM 2002.

Note that the ink cartridge 1906 and printhead 1903 are separable in the arrangement shown in FIG. 19, but may be integrated to configure an interchangeable head cartridge.

A droplet to be discharged from the printhead is ink, and a liquid contained in the ink tank is ink. However, the content is not limited to ink. For example, the ink tank may contain a processing liquid to be discharged to a sheet in order to improve the fixation and water resistance of a printed image and improve the image quality.

The inkjet printing apparatus adopts an arrangement (for example, an electrothermal transducer and laser beam) which generates thermal energy as energy used to discharge ink. By using the method of changing the ink state by thermal energy, the printing density and resolution can be increased.

The inkjet printing apparatus may employ a full-line type printhead having a length corresponding to the maximum width of a sheet, which is configured by combining a plurality of printheads to satisfy the length, or as one integrated printhead.

The printhead is not limited to a cartridge type printhead integrated with an ink tank, and may be an interchangeable chip type printhead which is mounted on the apparatus main body and can be electrically connected to the apparatus main body and receive ink from it.

The inkjet printing apparatus in the embodiment may take the form of an inkjet printing apparatus integrally or separately arranged as the image output terminal of an information processing apparatus such as a computer, the form of a copying apparatus combined with a reading apparatus, or the form of a facsimile apparatus having transmission and reception functions.

<Other Embodiments>

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-072338, filed Mar. 27, 2012, which is hereby incorporated by reference herein in its entirety.

What is claimed is:

1. A colorimetric apparatus comprising:
   an irradiation unit configured to irradiate a sheet selectively with visible light and ultraviolet light;
   a measurement unit configured to measure a spectral reflectance based on light reflected by the sheet; and
   a determination unit configured to determine, based on a spectral reflectance of a reference on the sheet that is measured by said measurement unit during an emission of the ultraviolet light, whether to cause said irradiation unit to emit the ultraviolet light when measuring a spectral reflectance of each of color patches on the sheet, wherein, said irradiation unit includes a first ultraviolet light source and a second ultraviolet light source having a wavelength different from that of the first ultraviolet light source, and wherein, in a case where the spectral reflectance of the reference contains a wavelength region of visible light, said measurement unit measures each of the color patches on the sheet by the first ultraviolet light source and the second ultraviolet light source respectively.

2. The apparatus according to claim 1, wherein said irradiation unit emits the visible light when measuring a spectral reflectance of each of the color patches on the sheet in a case where the spectral reflectance of the reference does not contain the wavelength region of the visible light.

3. The apparatus according to claim 1, wherein said determination unit determines whether the sheet contains a fluorescent brightener, based on whether the spectral reflectance of a reference image of color of the sheet contains the wavelength region of the visible light.

4. A printing apparatus comprising:
a colorimetric apparatus defined in claim 1; and
a printing unit which prints an image on a sheet.

5. A colorimetric method comprising:
measuring a spectral reflectance of a reference on a sheet with a first ultraviolet light and then, with a second ultraviolet light having a wavelength different from that of the first ultraviolet light;

determining whether the sheet contains a fluorescent brightener, based on whether the measured spectral reflectance contains a wavelength region of visible light; and, in a case where the sheet does not contain the fluorescent brightener, measuring a spectral reflectance of each of color patches on the sheet with the visible light, whereas in a case where the sheet contains the fluorescent brightener, measuring a spectral reflectance of each of the color patches with the visible light, the first ultraviolet light and the second ultraviolet light.

6. The method according to claim 5, further comprising adding measurement results of the spectral reflectance of the first ultraviolet light and the second ultraviolet light to each other.

* * * * *